(12) United States Patent
Menzel (10) Patent No.: US 8,800,842 B2
(45) Date of Patent: Aug. 12, 2014

(54) INTERNAL GASTRIC BANDER FOR OBESITY

(75) Inventor: Thomas E. Menzel, Tomah, WI (US)

(73) Assignee: Thomas E. Menzel, Pine Ridge, SD (US)

( * ) Notice: Subject to any disclaimer, the term of this patent is extended or adjusted under 35 U.S.C. 154(b) by 378 days.

(21) Appl. No.: 13/234,965

(22) Filed: Sep. 16, 2011

(65) Prior Publication Data

US 2012/0067937 A1    Mar. 22, 2012

Related U.S. Application Data (60) Provisional application No. 61/384,034, filed on Sep. 17, 2010.

(51) Int. Cl.
| A61B 17/04 | (2006.01) |
| A61F 5/00 | (2006.01) |
| A61B 17/072 | (2006.01) |
| A61B 17/064 | (2006.01) |
| A61B 17/068 | (2006.01) |
| A61B 17/00 | (2006.01) |
| A61B 17/115 | (2006.01) |

(52) U.S. Cl.
CPC ..... A61F 5/0089 (2013.01); A61B 2017/00323 (2013.01); A61B 2017/00314 (2013.01); A61F 5/0086 (2013.01); A61B 17/072 (2013.01); A61B 2017/1157 (2013.01); A61B 17/0644 (2013.01); A61B 17/0684 (2013.01)
USPC ........... 227/179.1; 227/19; 606/142; 606/219

(58) Field of Classification Search
USPC .............. 227/179.1, 19, 175.1; 606/151–153, 606/142, 219; 600/37
See application file for complete search history.

(56) References Cited

U.S. PATENT DOCUMENTS

| 5,588,579 A | * | 12/1996 | Schnut et al. ............... 227/175.1 |
| 6,149,658 A | * | 11/2000 | Gardiner et al. .............. 606/139 |
| 6,152,937 A | * | 11/2000 | Peterson et al. .............. 606/153 |
| 6,254,642 B1 | * | 7/2001 | Taylor ........................ 623/23.64 |
| 6,454,642 B1 | * | 9/2002 | Fierus et al. .................. 451/519 |
| 6,558,429 B2 | | 5/2003 | Taylor |
| 6,716,243 B1 | * | 4/2004 | Colvin et al. .................. 623/2.4 |
| 6,740,028 B2 | * | 5/2004 | Boone et al. .................... 600/37 |

(Continued)

FOREIGN PATENT DOCUMENTS

| WO | WO 03/090630 A2 | 11/2003 |
| WO | WO 2004/008936 A2 | 1/2004 |

(Continued)

*Primary Examiner* — Andrew M Tecco
*Assistant Examiner* — Chase Wilkins
(74) *Attorney, Agent, or Firm* — Charles S. Sara, Esq.; Daniel A. Blasiole; DeWitt Ross & Stevens SC (57) ABSTRACT

A non-surgical gastric bander device and process is described. The non-surgical gastric bander device includes a staple device, an elongated articulated shaft, an operations handle and a cable connecting the operations handle to the staple device. The staple device includes a housing having an interior housing channel for receiving a slidable tube. The slidable tube includes at least one suction port, a constriction band surrounding the exterior surface of the slidable tube and a plurality of staples removably positioned adjacent the exterior surface of the slidable tube and held in place by the constriction band. The gastric bander device further includes an elongated, articulated shaft connecting the staple device to an operations handle.

17 Claims, 11 Drawing Sheets

(56) References Cited

U.S. PATENT DOCUMENTS

| | | | |
|---|---|---|---|
| 6,872,214 B2* | 3/2005 | Sonnenschein et al. | 606/153 |
| 6,884,250 B2 | 4/2005 | Monassevitch et al. | |
| 6,911,042 B2* | 6/2005 | Weadock | 623/1.23 |
| 6,957,758 B2* | 10/2005 | Aranyi | 227/176.1 |
| 6,966,917 B1* | 11/2005 | Suyker et al. | 606/148 |
| 7,018,387 B2* | 3/2006 | Suyker et al. | 606/153 |
| 7,087,088 B2* | 8/2006 | Berg et al. | 623/23.64 |
| 7,141,055 B2* | 11/2006 | Abrams et al. | 606/115 |
| 7,159,750 B2* | 1/2007 | Racenet et al. | 227/180.1 |
| 7,220,237 B2 | 5/2007 | Gannoe et al. | |
| 7,311,730 B2* | 12/2007 | Gabbay | 623/2.38 |
| 7,422,138 B2 | 9/2008 | Bilotti et al. | |
| 7,611,535 B2* | 11/2009 | Woolfson et al. | 623/2.38 |
| 7,666,198 B2* | 2/2010 | Suyker et al. | 606/153 |
| 7,674,271 B2 | 3/2010 | Bjerken | |
| 7,802,712 B2* | 9/2010 | Milliman et al. | 227/176.1 |
| 7,841,503 B2 | 11/2010 | Sonnenschein et al. | |
| 8,012,135 B2* | 9/2011 | Dann et al. | 604/263 |
| 2003/0055441 A1* | 3/2003 | Suyker et al. | 606/153 |
| 2003/0216778 A1* | 11/2003 | Weadock | 606/219 |
| 2004/0092960 A1* | 5/2004 | Abrams et al. | 606/139 |
| 2004/0167549 A1* | 8/2004 | Boone et al. | 606/151 |
| 2005/0055038 A1 | 3/2005 | Kellcher et al. | |
| 2006/0079917 A1 | 4/2006 | Nicolo | |
| 2007/0038230 A1 | 2/2007 | Stone et al. | |
| 2007/0123994 A1 | 5/2007 | Ortiz et al. | |
| 2007/0198034 A1 | 8/2007 | Ortiz et al. | |
| 2007/0233162 A1 | 10/2007 | Gannoe et al. | |
| 2007/0276432 A1 | 11/2007 | Stack et al. | |
| 2008/0132925 A1 | 6/2008 | Demarais | |
| 2008/0172074 A1 | 7/2008 | Baker et al. | |
| 2009/0001125 A1* | 1/2009 | Hess et al. | 227/176.1 |
| 2009/0182352 A1* | 7/2009 | Paz et al. | 606/143 |
| 2009/0192531 A1 | 7/2009 | Hsu et al. | |
| 2010/0069931 A1 | 3/2010 | Baker et al. | |
| 2010/0076451 A1 | 3/2010 | Zwolinski et al. | |
| 2010/0076466 A1* | 3/2010 | Yasuda | 606/153 |

FOREIGN PATENT DOCUMENTS

| | | |
|---|---|---|
| WO | WO 2005/084592 A2 | 9/2005 |
| WO | WO 2005/115255 A1 | 12/2005 |
| WO | WO 2008/108936 A1 | 9/2008 |

* cited by examiner

INTERNAL GASTRIC BANDER FOR
OBESITY

CROSS-REFERENCE TO RELATED APPLICATION

The application claims priority to U.S. Provisional Application entitled "INTERNAL GASTRIC BANDER FOR OBESITY," Ser. No. 61/384,034, filed Sep. 17, 2010, which is incorporated herein by reference in its entirety.

FIELD OF THE INVENTION

The present invention is directed to the treatment of obesity. The present invention is particularly directed to a removable banding device for constricting the stomach.

BACKGROUND

Obesity, defined as having an excessive amount of body fat, has been linked with an increased risk of health problems such as diabetes, high blood pressure, and more recently cancer. The body mass index ("BMI") is often used to determine whether a person is obese. A normal BMI is between 18.5 and 25, while a BMI of 30 or greater in adults is considered obese. Morbid obesity (also known as extreme obesity or severe obesity) is associated with a BMI of 40 or greater, and it greatly increases the risk of serious health problems. Surgery for morbid obesity has been shown to decrease the risks of diabetes and cancer, and the prevalence of such surgery is expected to increase in coming years.

Currently there are two major surgical operations for aiding weight loss that are performed laparoscopically: Roux-en-Y gastric bypass and laparoscopic gastric banding. In gastric bypass surgery, the stomach is divided and a proximal gastric pouch is connected by a small bowel Roux-en-Y limb, resulting in weight loss by causing satiety and possibly malabsorption. Although it results in weight loss, a high percentage of patients regain weight after two years.

In laparoscopic gastric banding, a surgeon positions an adjustable band around the upper part of the stomach to form a small pouch which holds food. Gastric banding most likely works by restricting solids and increasing pressure in the gastric cardia, leading to the patient feeling sated and decreasing oral consumption. Gastric banding allows the gut to maintain its original architecture, and the procedure is reversible by removal of the gastric band. It does, however, have other complications such as slippage and erosion of the band.

The shortcomings of today's technology (such as gastric banding and gastric bypass) include its invasiveness, requiring an operation with significant morbidity and mortality for the patient. It is also expensive and time consuming, requiring complex surgery to reverse. These shortcomings contribute to the reluctance of those who are morbidly obese to undergo current procedures. What is needed is a treatment that is effective, has a low morbidity, is reversible, is inexpensive, and is quick to perform.

SUMMARY OF THE INVENTION

The present invention is directed to a non-surgical process for applying a gastric band to the stomach. More specifically, the present invention is directed to a gastric bander staple device comprising a housing having a first end and a second end and an interior housing channel; a slidable tube for slidable reception within the interior housing channel, the slidable tube having a first end, a second end, an exterior surface and an interior surface forming an open tube channel within the slidable tube; at least one suction port comprising an opening from the exterior surface of the slidable tube to the tube channel; a constriction band surrounding the exterior surface of the slidable tube; a plurality of staples removably positioned adjacent the exterior surface of the slidable tube and held in place by the constriction band; and an anvil removably positioned on the first end of the slidable tube, the anvil including a first upper surface and a second lower surface, wherein the second lower surface has a shape substantially similar to the first end of the slidable tube, the anvil further including a guide edge for the plurality of staples.

The present invention is also directed to a non-surgical gastric bander comprising a staple device including a housing having a first end and a second end and an interior housing channel, wherein the first end of the housing comprises a staple ring comprising outwardly extending staple grooves; a slidable tube for slidable reception within the interior housing channel and having a first end, a second end, an exterior surface and an interior surface forming an open tube channel within the slidable tube, wherein the slidable tube includes a plurality of staple grooves, each staple groove adapted to removably receive a staple; at least one suction port comprising an opening from the exterior surface of the slidable tube to the tube channel; a constriction band surrounding the exterior surface of the slidable tube; a plurality of staples removably positioned adjacent the exterior surface of the slidable tube and held in place by the constriction band; and an anvil removably positioned on the first end of the slidable tube, the anvil including a first upper surface and a second lower surface, wherein the second lower surface has a shape substantially similar to the first end of the slidable tube, the anvil further including a guide edge for the plurality of staples. The gastric bander further includes an elongated, articulated shaft having a proximal end and a distal end, wherein the proximal end is connected to the first end of the housing, and the articulated shaft is surrounded by an air impervious membrane. The gastric bander further includes an operations handle connected to the distal end of the articulated shaft, the operations handle comprising a suction port for attachment to a gas suction device and a cable having a proximal end and a distal end, wherein the proximal end is connected to the anvil and the distal end is connected to the operation handle. Finally, the gastric bander includes means within the operations handle for extending and constricting the cable.

The present invention also comprises an articulated shaft having a proximal and a distal end comprising a plurality of adjacent links, wherein each link is pivotally attached to an adjacent link in a manner to allow limited pivoting movement of the shaft in both an X and a Y axis. Each link comprises an outer surface, an inner surface forming an interior passageway, an upper first surface comprising an arched protrusion including a pair of outwardly extending lips, and a lower second surface comprising an arched notch comprising a pair of inwardly depending edges wherein the pair of outwardly extending lips of the upper first surface are formed to receive the pair of inwardly depending edges of the next adjacent link in a snap fit fashion to connect each adjacent link in a manner allowing limited pivoting movement of the connected adjacent links in both an X and a Y axis. The articulated shaft further comprises a cable having a proximal and a distal end, wherein the proximal end of the cable is connected to a stopper mechanism at the proximal end of the articulated shaft and the distal end is connected to a means for extending or constricting the cable, wherein the constriction of the cable prevents pivotal movement of adjacent links with respect to each other and the extension of the cable allows pivotal movement of adjacent links.

Advantageously, the gastric bander device is completely sealed to allow the device to create a suction which deflates the stomach. Once the stomach is deflated, the constriction band can be stapled onto the inner wall of the stomach in order to divide the stomach into a smaller pouch which will simulate the stomach and give the patient an earlier feeling of being full. Because the constriction band is attached to the interior of the stomach wall by the action of the staples, this procedure is known as a non-surgical procedure. In addition, it is relatively easy to reverse the process by simply snipping the band.

Other advantages of the device of the present invention include the fact that the present invention does not require a general anesthetic and that it does not involve incisions to the skin. The entire procedure can be accomplished under mild sedation endoscopically and is relatively quick to perform. In addition, the removal procedure can be accomplished under mild sedation in a relatively quick time, i.e., 15 minutes or less. The procedure can be performed with the skills of a gastroenterologist and does not require a surgeon for placement or removal. Finally, because the constriction band is not fixed to the stomach tissue, the procedure is readily reversible by cutting the band.

The objects and advantages of the invention will appear more fully from the following detailed description of the preferred embodiment of the invention made in conjunction with the accompanying drawings.

DETAILED DESCRIPTION OF THE INVENTION

The present invention is directed to an internal treatment for morbid obesity. In an exemplary version, a portion of the stomach 100 is constricted internally by stapling a constriction band 54 to the inside of the stomach 100.

Figure 1:
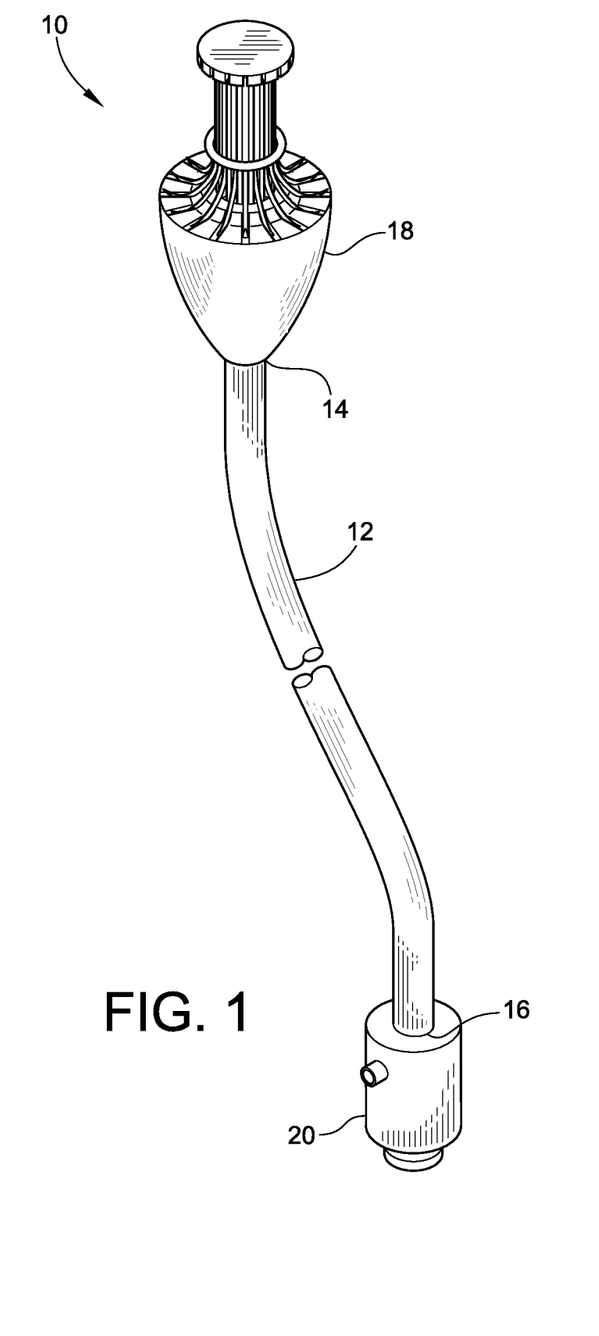
FIG. 1 is a perspective view of the gastric bander device of the present invention.

With reference to FIG. 1, this procedure is accomplished by a gastric bander device 10, which is comprised of an elongated articulated shaft 12 having a proximal end 14 and a distal end 16. Located at the proximal end 14 is a staple device 18. Located at the distal end 16 is the operations handle 20. The purpose of the gastric bander device 10 is to place the staple device 18 within the stomach 100 by urging the device 10 through the esophagus 98 utilizing the lateral motion of the articulated shaft 12. Once the staple device 18 is placed within the stomach 100, it can be activated to "band" the stomach 100 wall to provide constriction. This process is described with reference to FIGS. 9-13.

Figure 2:
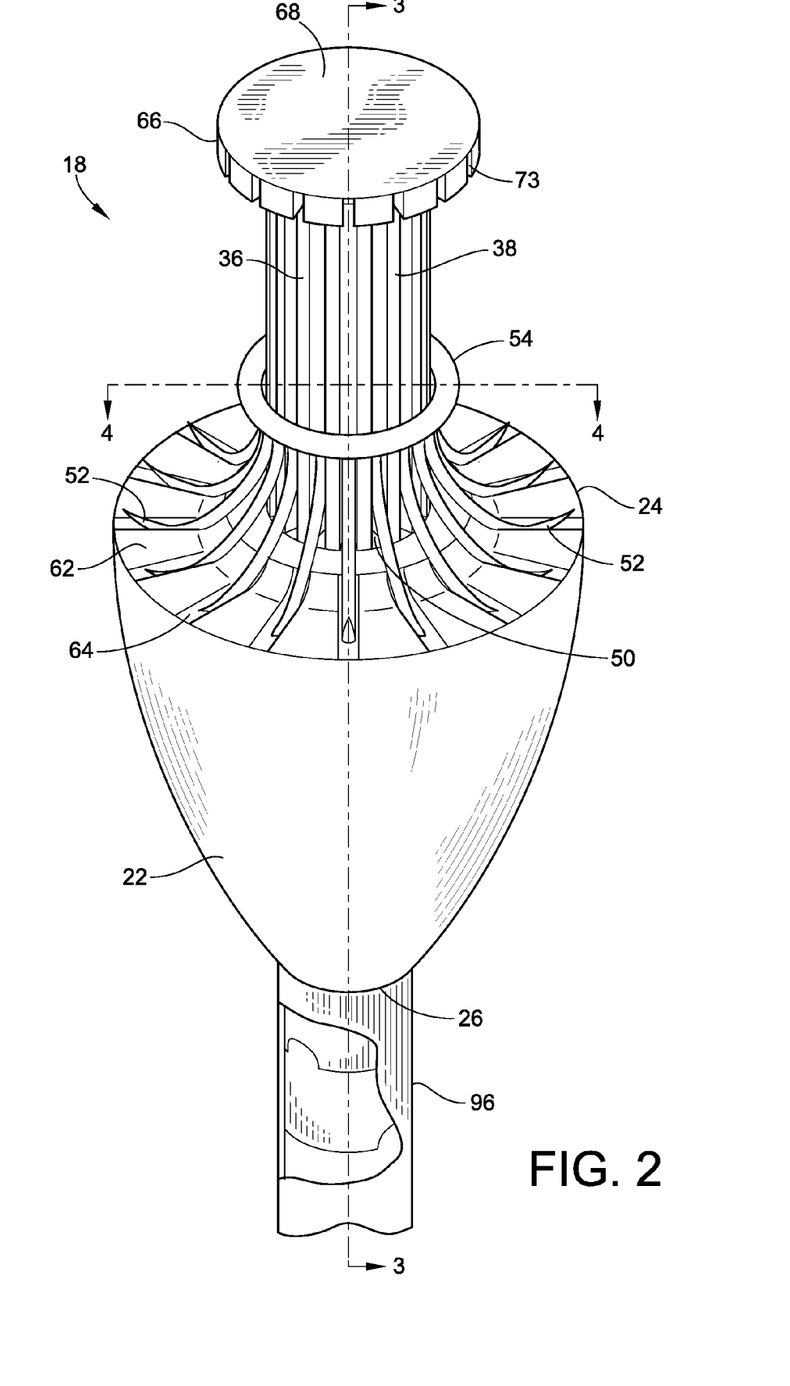
FIG. 2 is a perspective view of the staple device of the gastric bander of FIG. 1.
Figure 3:
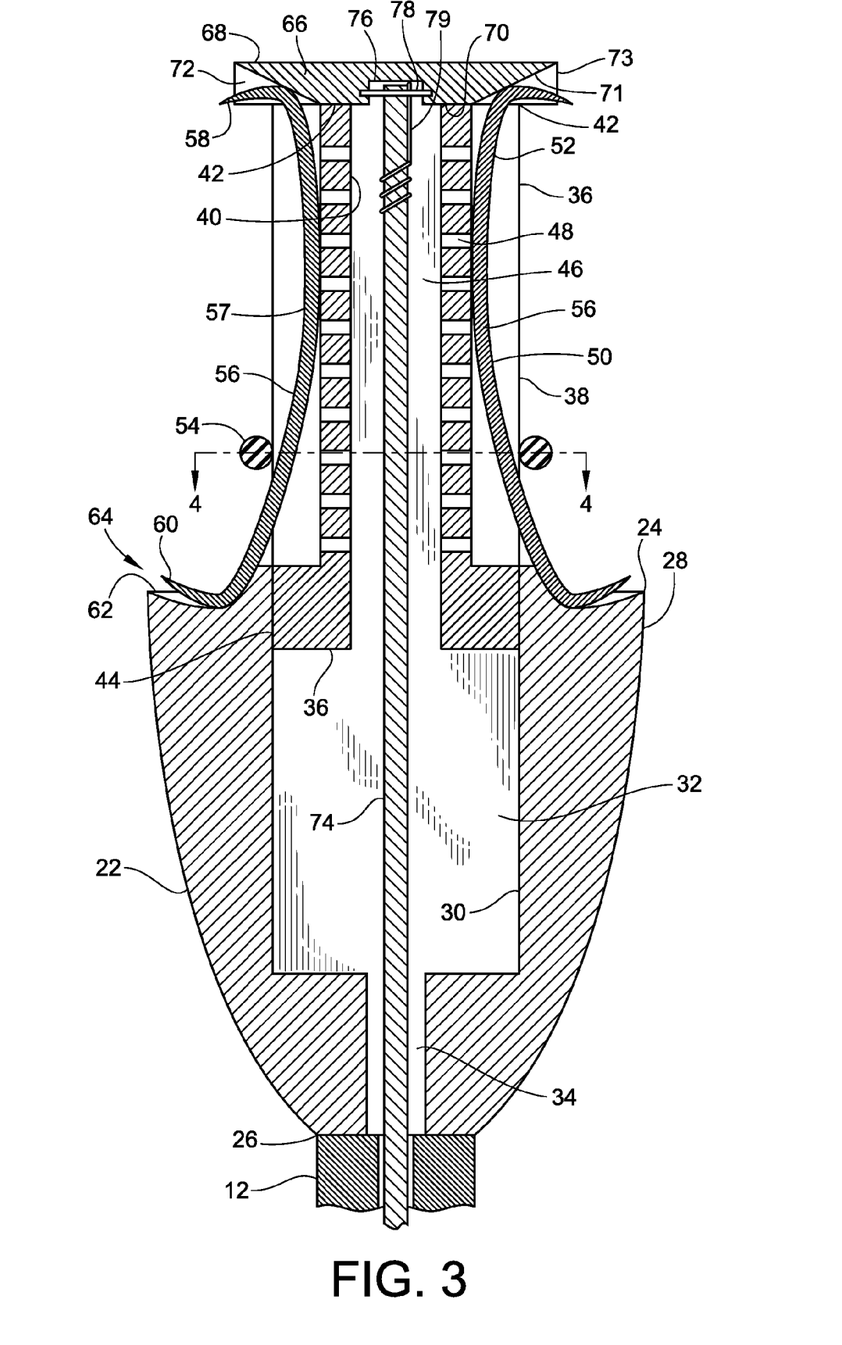
FIG. 3 is a cross-sectional view of the staple device of FIG. 2 taken along lines 3-3 of FIG. 2.
Figure 4:
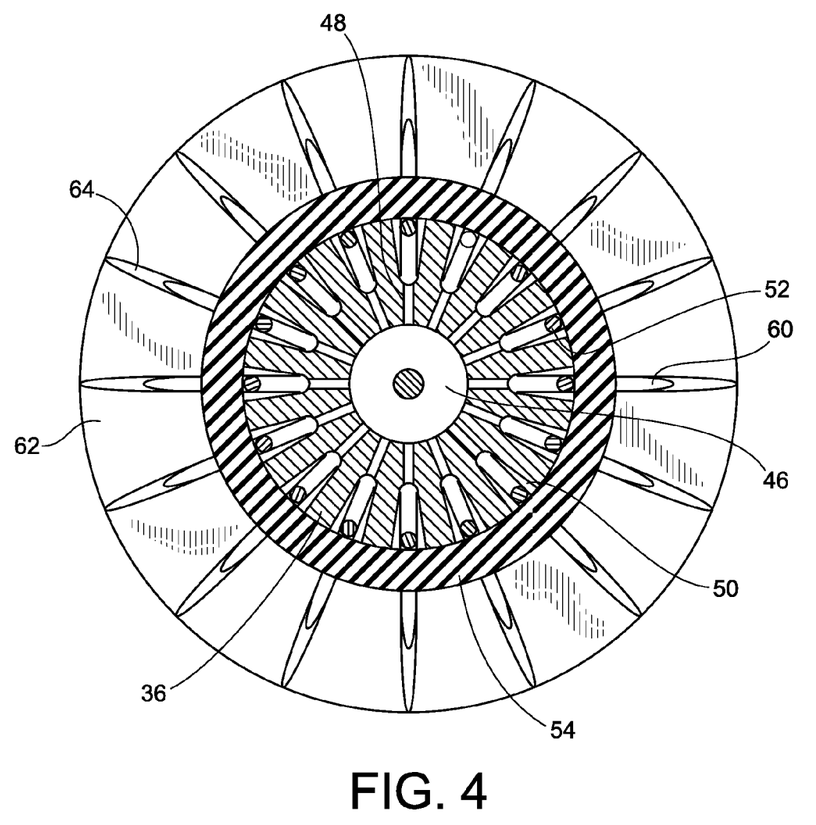
FIG. 4 is a cross-sectional view of the staple device of FIGS. 2 and 3 taken along lines 4-4 of FIGS. 2 and 3.

Reference is now made to FIGS. 2-4 which illustrate the staple device 18. The staple device 18 includes a conically-shaped housing 22 having an upper end 24 and a second lower end 26. Referring to FIG. 3, the housing 22 includes an outer wall 28 and an interior wall 30 which forms the interior housing channel 32. As illustrated in FIG. 3, the interior housing channel 32 reduces in diameter near the second lower end 26 to form a cable channel 34. Located near the upper end 24 of the housing 22 is a slidable tube 36 generally of cylindrical shape. The slidable tube 36 is defined by an exterior surface 38, an interior surface 40, an upper first end 42 and a lower second end 44, illustrated in FIG. 3. As illustrated in FIGS. 3 and 4, the interior surface 40 defines an open tube channel 46.

Located on the slidable tube 36 are a plurality of suction ports 48 which comprise an opening from the exterior surface 38 of the slidable tube 36 to the tube channel 46. In addition, the suction ports 48 are located within staple grooves 50, which are grooves or troughs located within the exterior surface 38 of the slidable tube 36 for removably positioning a plurality of staples 52. The staples 52 are positioned and secured within the staple grooves 50 of the slidable tube 36 by means of a constriction band 54 preferably positioned at the lower third or fourth of the slidable tube 36 as illustrated in FIGS. 2 and 3. While the preferred positioning of the constriction band 54 is below the midpoint of the slidable tube 36 as illustrated, it is within the scope of the present invention to position the constriction band 54 at the midpoint of the slidable tube 36 or higher. The constriction band 54 holds the staples 52 in place in the staple grooves 50 on the slidable tube 36. In this manner, the constriction band 54 will function to hold the staples 52 on the slidable tube 36 until deployment. After deployment of the staples 52 into the stomach 100, the constriction band 54 functions to constrict the stomach 100 thereby creating a pouch 124 in the upper wall of the stomach 100 (see FIG. 15). The constriction band 54 is preferably made of polypropylene but may be made of other materials such as fluorocarbon or SILASTIC (Dow Corning, Germantown, Wis.) which may offer the advantage of some elasticity, but may not be as durable as polypropylene. The diameter of the constriction band 54 will be approximately 1 centimeter to allow for passage of an endoscope (not illustrated) into the stomach 100 after the staple device 18 has been placed into the stomach 100 for observation to ensure the integrity of the deployed constriction band 54, but may be larger or smaller as dictated by the need to control obesity.

As perhaps best illustrated in FIG. 3, the staple 52 is an elongated structure typically made of metal, such as stainless steel, titanium or other metals known to the art. The staple 52 will be required to bend at its mid portion, i.e., at the area of constriction by the constriction band 54 which may be facilitated by a thinner cross section at the midpoint 57 of the staple 52 as compared to the rest of the staple 52 or by case hardening the ends 58, 60 of the staple 52 or both, when the staple device 18 is activated. As illustrated in FIG. 3, the shaft 56 of the staple 52 has an elongated, flattened but slightly arcuate shape ending at either end by staple points at each of the upper end 58 and lower end 60 of the staples 52. The staple points are at an approximate 90° angle from the shaft 56. The lower end 60 of each staple 52 is positioned in a circular staple ring 62 at the first end 24 of the housing 22. As discussed above, the midpoint 57 of the shaft 56 is slightly thinner than the rest of the shaft to create an area of bend in the staple 52. As illustrated in FIG. 4, the staple ring 62 is defined by outwardly elevating grooves 64, each of which are designed to position the lower end 60 of the staple 52.

Located at the upper first end 42 of the slidable tube 36, is a disk-shaped anvil 66 which is removably positioned on the upper first end 42 of the slidable tube 36. Without wishing to be restricted to any particular shape, it is presumed that the preferred shape for the present invention will be a circular disk having a first upper surface 68 and second lower surface 70. The anvil 66 is somewhat conically shaped wherein the lower surface 70 has a circumference approximately the same circumference as the outer diameter of the slidable tube 36. The upper surface 68 of the anvil 66 has a larger circumference. For this reason, there is a beveled edge 71. The lower surface 70 of the anvil 66 is defined by a plurality of radially oriented staple grooves 72. These staple grooves 72 originate at approximately the outer diameter of the slidable tube 36, as illustrated in FIG. 3, and extend outward becoming deeper to involve almost the full thickness of the anvil 66 as the staple grooves 72 approach the edge of the upper surface 68 to act as a sliding guide for the upper end 58 of the staple 52 to enable each of the staples 52 to grasp onto the folds of the stomach 100 as the staple 52 is being bent into a clasping fashion. Each staple groove 72 terminates at a notch 73 at the edge of the anvil 66. This notch 73 is conveniently placed to assist in the movement and positioning of the staple 52 to its closed state when the slidable tube 36 slides within the interior housing channel 32.

The diameter of the upper surface 68 of the anvil 66 is approximately 1.3-1.4 times larger than the diameter of the slidable tube 36 at its lower second end 44. Consequently, the diameter of the upper surface 68 of the anvil 66 is also approximately 1.3-1.4 times the resting internal diameter of the constriction band 54. The second lower surface 70 of anvil 66 is designed to be removably positioned upon the upper edge 42 of the slidable tube 36.

As illustrated in FIGS. 2 and 3, the staples 52 are canted slightly such that the lower end 60 of each staple 52 extends outwardly beyond the upper end 58. The purpose for this is to allow the anvil 66 to pass through the constriction band 54 to provide the desired stapling action as will be discussed in the following paragraphs.

Figure 14:
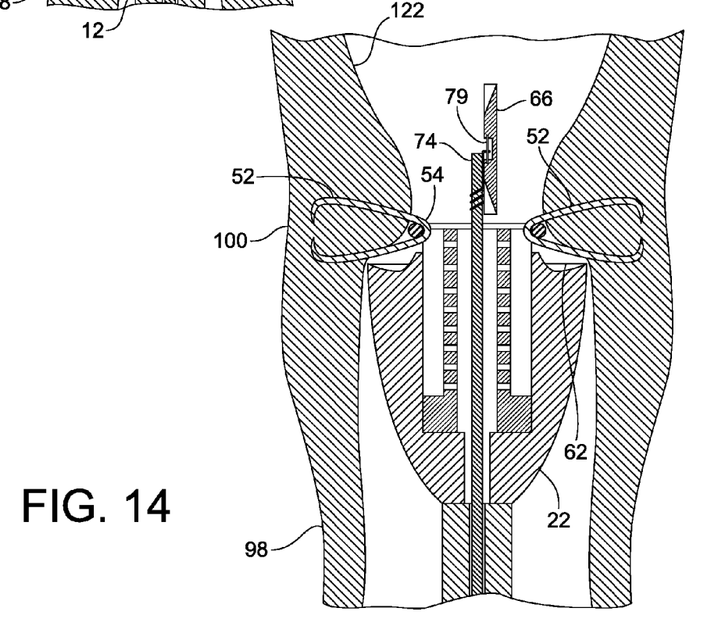
FIG. 14 illustrates the extension of the cable to elevate and rotate the anvil without deflation of the stomach.
Figures 15, 16:
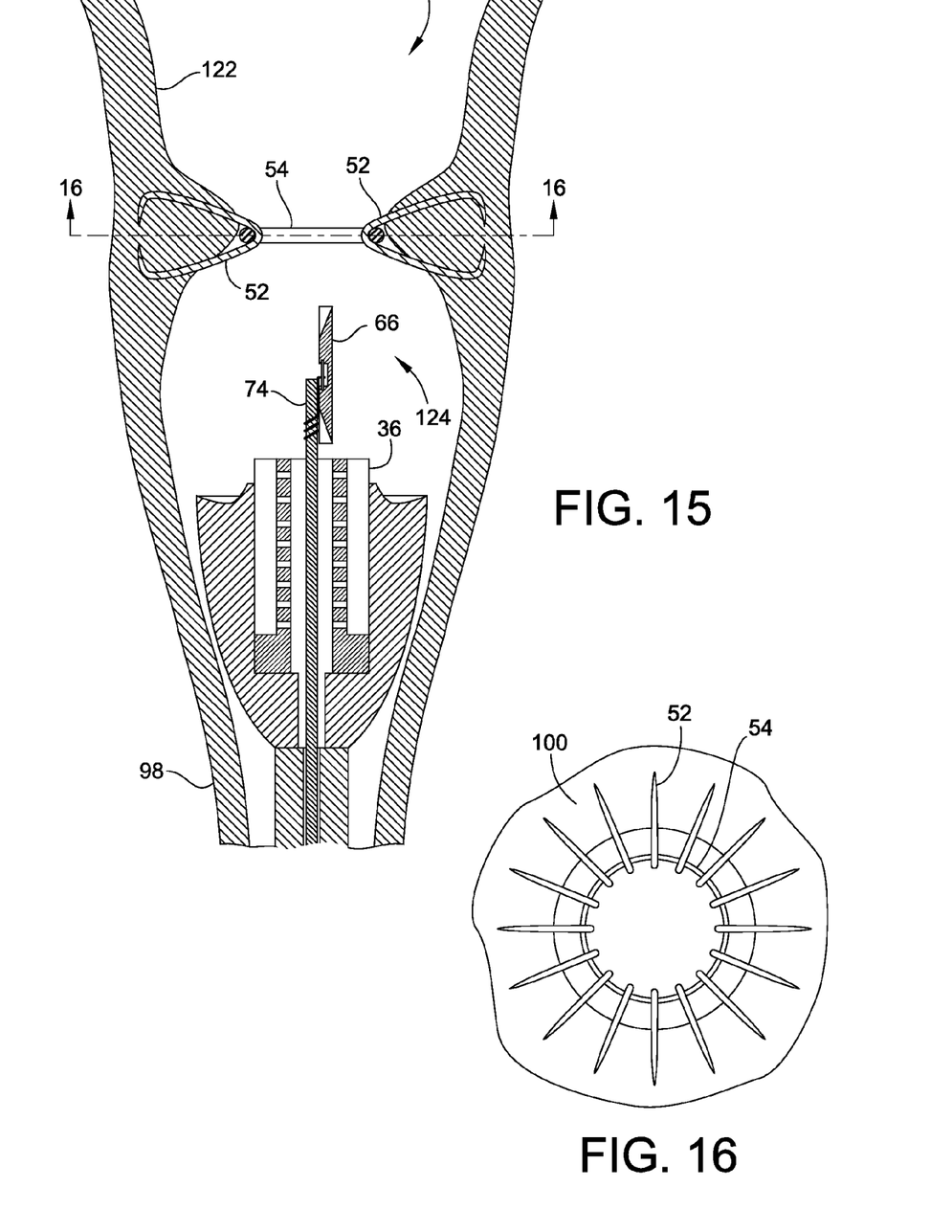
FIG. 15 illustrates the removal of the gastric bander device from the stomach.
FIG. 16 is a cross-section view of FIG. 15 taken along lines 16-16 of FIG. 15.

Finally with respect to the staple device 18, there is illustrated a central cable 74 which extends from an attachment device 76 of the anvil 66 through the tube channel 46, the interior housing channel 32 and ultimately through the center of the articulated shaft 12 to the operations handle 20 as will be described shortly. The proximal end 78 of the cable 74 is attached to the anvil 66 at the attachment point 76. Located on the cable 74 in the area of the proximal end 78 of the cable 74 is a compression spring 79 which is designed to urge the anvil 66 to rotate in a 90 degree angle such that the lower second surface 70 of the anvil 66 will rest alongside the surface of the cable 74 when the staple device 18 is removed from the stomach 100 after deployment of the constriction band 54, as illustrated in FIGS. 14 and 15.

Figure 5:
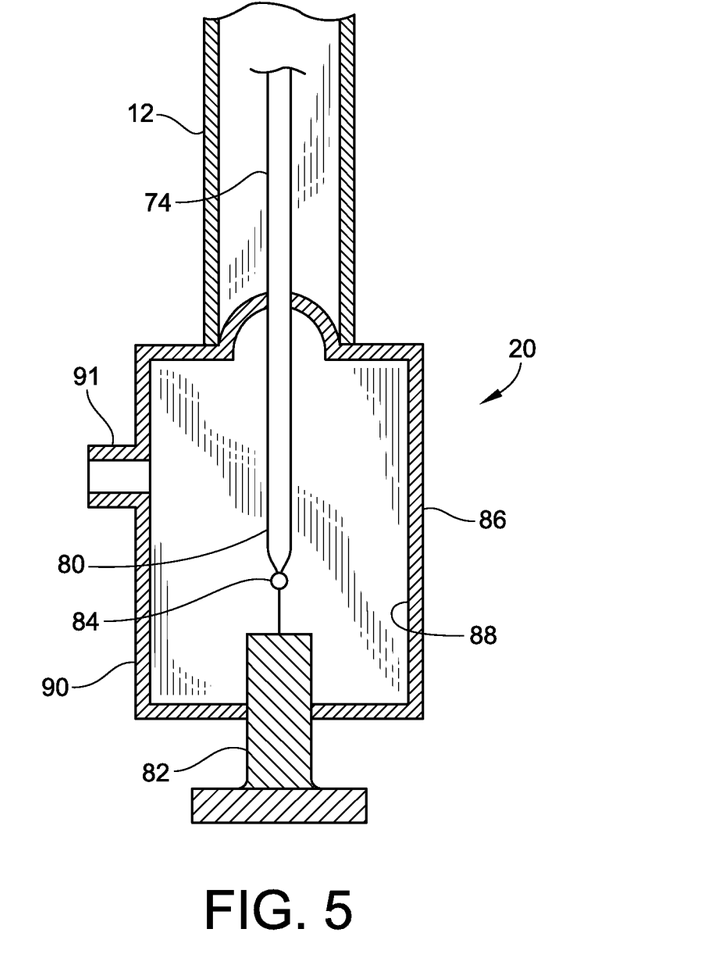
FIG. 5 is a cross-sectional view of the operations handle of the gastric bander of the present invention.

Referring now to FIG. 5, the operations handle 20 is seamlessly attached to the articulated shaft 12 by means known to the art, such as glue, or other sealing materials. In addition, the cable 74 traverses through the interior of the shaft 12 until the distal end 80 is attached to a turn screw 82 or the like at attachment mechanism 84. The purpose of the turn screw 82 is to lengthen or shorten the cable 74 within the articulated shaft 12. While a turn screw 82 is illustrated and described, it is well within the art to provide other means for extending and withdrawing the cable 74 within the articulated shaft 12. The operations handle 20 further includes a wall 86 having an interior surface 88 and an exterior surface 90. Further, a suction port 91 is illustrated for attachment to an air suction mechanism to create a vacuum within the entire gastric bander device 10 system from the operations handle 20 through the articulated shaft 12 and the gastric bander device 10 in order to deflate the stomach 100.

Figure 6:
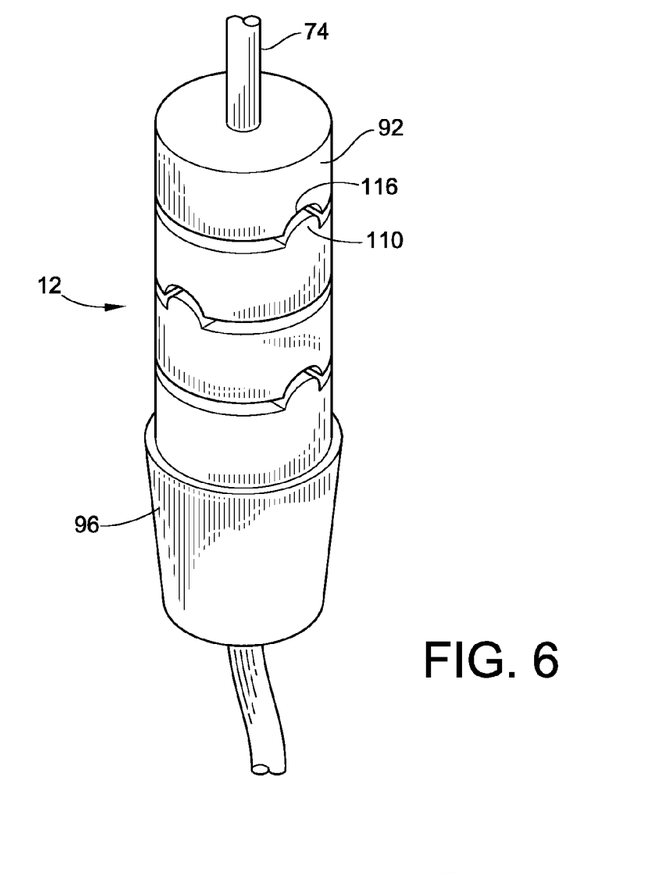
FIG. 6 is a partial, perspective view of the articulated shaft of the present invention.
Figure 7:
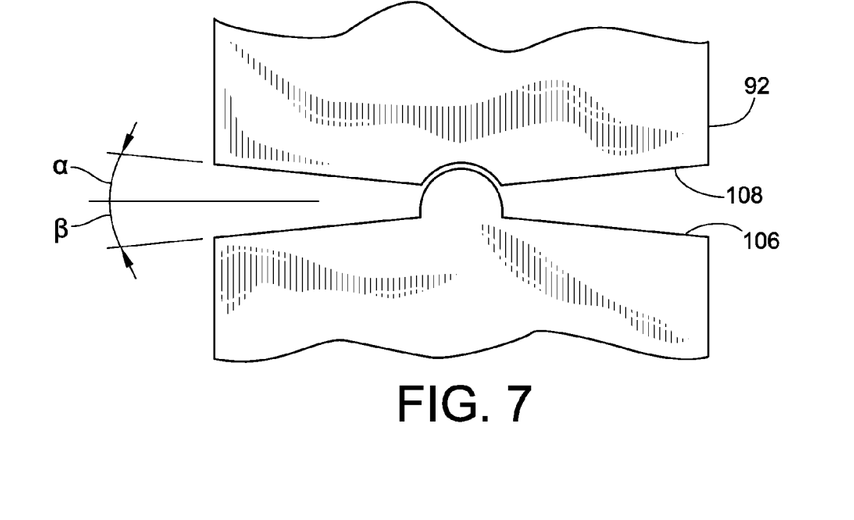
FIG. 7 is a partial side view of adjacent links of the articulated shaft of FIG. 6.
Figure 8A:
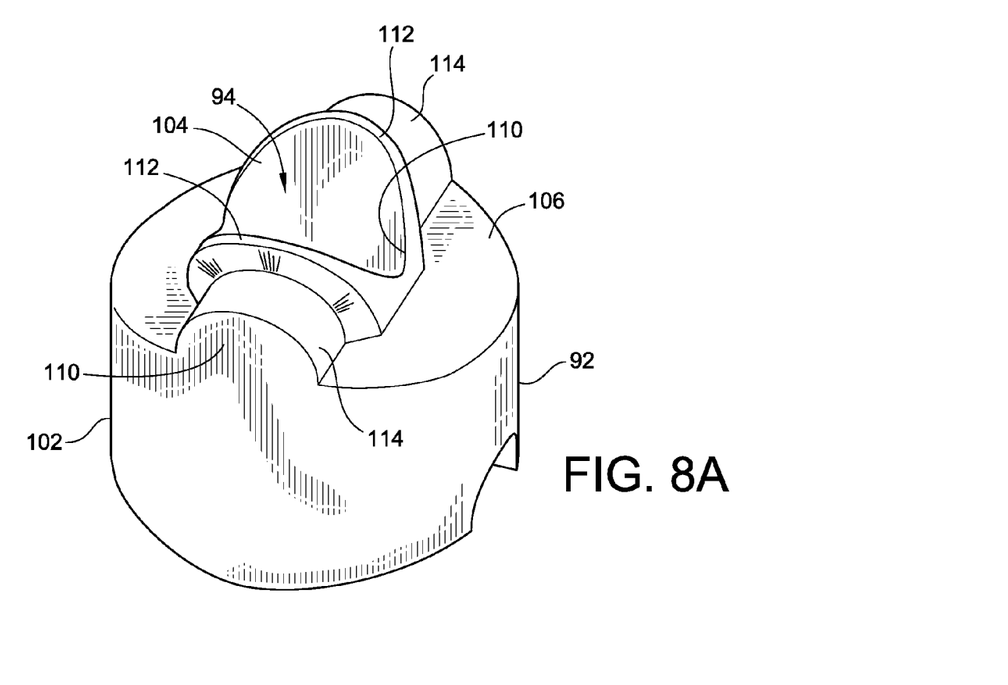
FIG. 8A is a perspective view illustrating the upper or dorsal end of a links of the articulated shaft of the present invention.
Figure 8B:
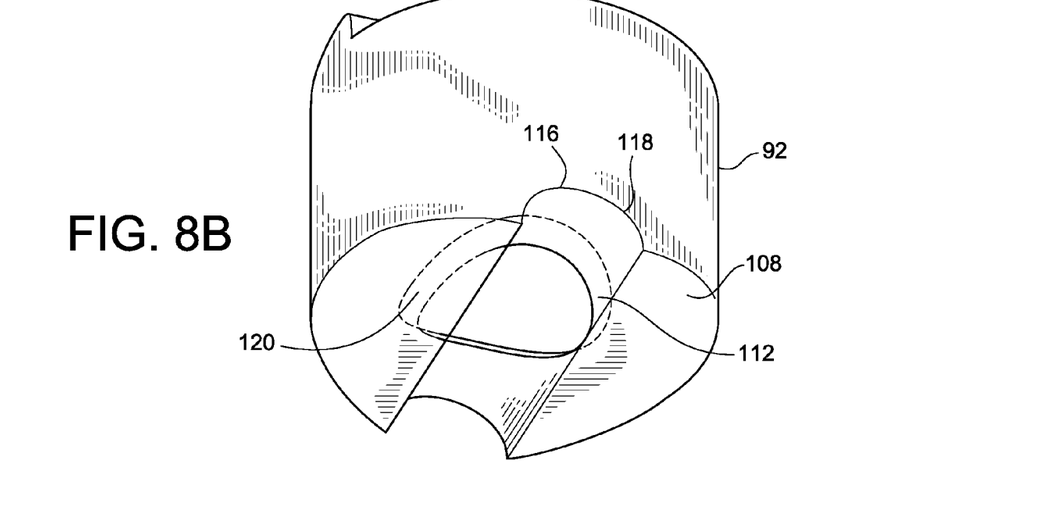
FIG. 8B is a perspective view illustrating the bottom or ventral side of a link of the articulated shaft of the present invention.
Figure 9:
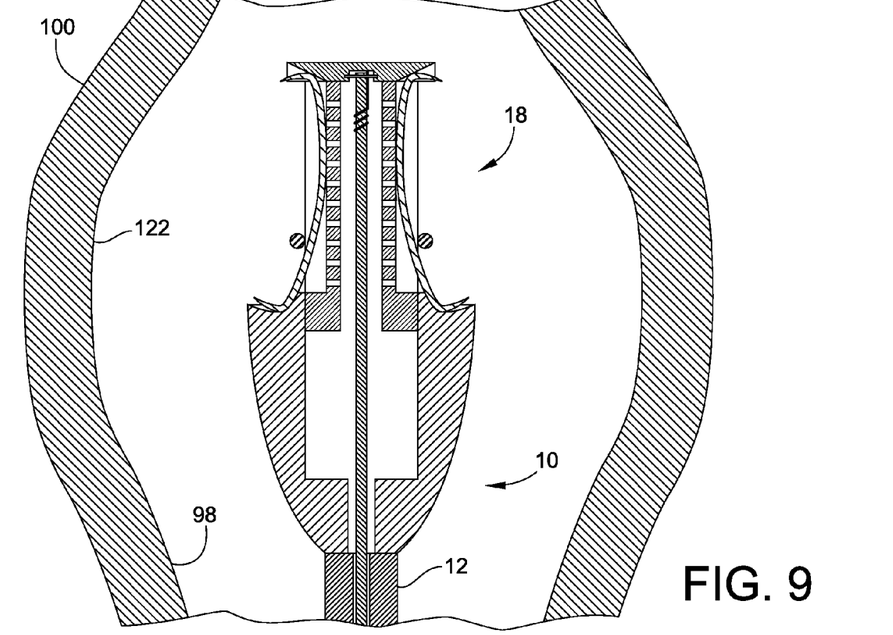
FIG. 9 illustrates the initial placement of the gastric bander device within the stomach.

Reference is now made to FIGS. 6-8 for a description of the articulated shaft 12. The articulated shaft 12 is an extended shaft connecting the lower end 26 of the housing 22 at its proximal end 14 to the operations handle 20 at the distal end 16 of the articulated shaft 12. While the articulated shaft 12 has a primary purpose in the invention to place the staple device 18 through the esophagus 98 and into the stomach 100 as illustrated in FIG. 9, the articulated shaft 12 can also have a variety of other medical and non-medical uses. The length of the articulated shaft 12 depends on its needs. For purposes of the present invention, the articulated shaft 12 can have a length of approximately 60 cm.

The articulated shaft 12 of the present invention may comprise three basic elements: (1) a plurality of adjacent links 92, (2) the cable 74 passing through an interior passageway 94 of the links 92, and (3) an outer or inner impermeable sheath 96 to seal the device. The cable 74 is a flexible cord, typically made of steel, plastic or other wire material. It is defined by the characteristics of being flexible to allow the plurality of links 92 to articulate. However, the cable 74 is also relatively inextensible. The cable 74 extends through the interior passageway 94 and assists with the manipulation of the articulated shaft 12 and the staple device 18 through the esophagus 98 to the stomach 100.

As illustrated in FIG. 6, the articulated shaft 12 is composed of the plurality of relatively loose-fitting cylindrical links 92 placed in series. An impermeable sheet 96 is then placed over the links 92. This creates a closed system which allows the suction apparatus to suction air and other gasses from the stomach 100.

Reference is now made to FIGS. 7, 8A and 8B for a more detailed description of the link 92. The link 92 is a generally cylindrical link defined by an outer surface 102 and an inner surface 104 which creates the interior passageway 94 through which the cable 74 extends. In addition, the link 92 includes an upper first surface 106 and a lower second surface 108. The upper first surface 106 is defined by an arched protrusion 110. The arched protrusion 110 is further defined by a pair of matched outwardly extending lips 112. The outwardly extending lips 112 are situated adjacent the arched surface 114 of the arched protrusion 110. The upper first surface 106 of the link 92 is beveled at a slight downward direction (angle β in FIG. 7) in order to accommodate the articulation of the next attached link. Likewise, the lower second surface 108 is either beveled (angle α in FIG. 7) or straight in order to provide a slight gap to allow an articulated movement between the links 92 when they are attached. The desired beveling can be reversed as long as there is sufficient "play" between the adjacent links 92 to allow articulated movement.

Situated at the lower second surface 108 is an arched notch 116 which further defines a notched surface 118. The interior walls 120 of the arched notch 116 are defined by inwardly depending interior wall 120 to accommodate the outwardly extending lips 112 of the next link 92. In this manner, each link 92 will snap fit in a continuous link formation by the action of the outwardly extended lips 112 of one link 92 being press fit into an inwardly depending interior wall 120 of the adjacent link 92. Once linked together, these links 92 can articulate in a slight angular fashion. The first link 92 will then be able to move slightly in an X direction. The next link 92, because of the positioning of the lips 112 and the edges of the interior walls 120 will articulate in a slight Y direction giving the articulated shaft 12 an articulated mobile movement.

The interior placed cable 74 serves to stiffen the articulated shaft 12 as necessary. This is accomplished by the anvil 66, which is attached to the proximal end 78 of the cable 74 at attachment point 76. If the articulated shaft 12 will be used for another purpose, it is assumed that a stopper having the same purpose as the anvil 66 will be substituted for the anvil 66. If the cable 74 is withdrawn and shortened by the action of the operations handle 20, the anvil 66 will press onto the slidable tube 36 of the staple device 18 which then compresses each individual link 92 upon the next link 92 in line. This compression will cause the articulated shaft 12 to lock or freeze in a desired set position. While not necessary, it is preferred that the upper first surface 114 and/or the notched surface 118 of the link 92 have a roughened or knurled surface in order to assist with the positioning of the articulated shaft 12 when the cable 74 is shortened.

In this manner, the articulated shaft 12 can be loosened by extension of the cable 74 to allow full articulated motion as the articulated shaft 12 is being guided down the esophagus 98 and into the stomach 100 of the patient. Once the proper positioning has been made, the cable 74 can be shortened or contracted which compresses each link 92 of the articulated shaft 12. This compression will cause the articulated shaft 12 to freeze in the current configuration. In this manner, the bending operation can occur without slippage on behalf of the articulated shaft 12.

Thus, the articulated shaft 12 provides the necessary length to position the staple device 18 within the stomach 100. The articulated shaft 12 must also be flexible to enable the movement of the staple device 18 through the esophagus 98 to the stomach 100. The articulated shaft 12 must also have the ability to attain the desired rigidity when the staple device 18 is about to commence operation. Further, the articulated shaft 12 must be air sealed to provide suction through the staple device 18 in order to collapse the stomach 100.

While the size of the links 92 may change depending on the use of the articulated shaft 12, for purposes of each of the present invention, each link 92 will have a diameter of approximately 1 centimeter. The individual links 92 can be made of a number of materials known to the art, such as plastic, polycarbonate, aluminum and polyvinyl chloride (PVC) to name a few. A preferred material for the purposes of the present invention is PVC. The links 92 may also be stamp molded and manufactured according to methods known to the art. A preferred method of manufacturing the links 92 is by injection molding.

Figure 10:
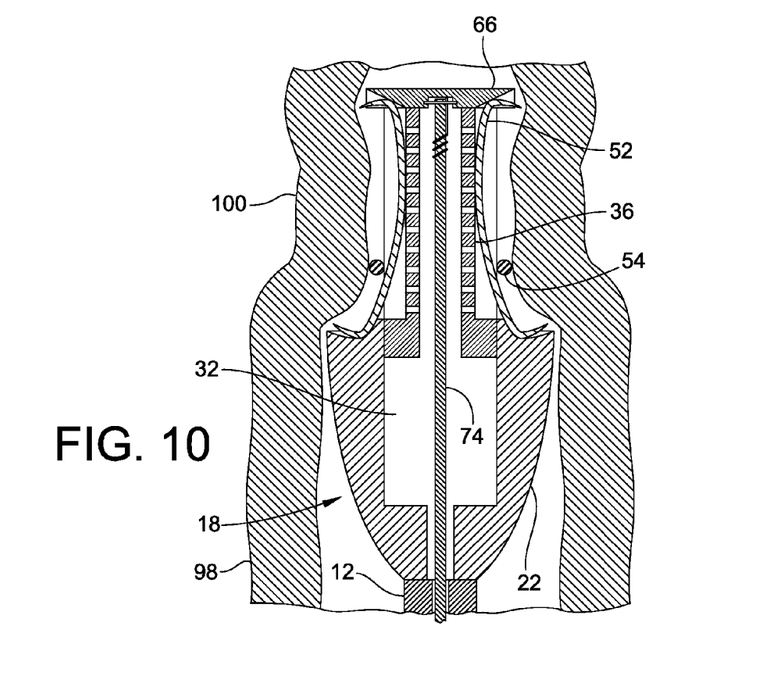
FIG. 10 illustrates the deflated stomach surrounding the gastric bander device of the present invention.
Figure 11:
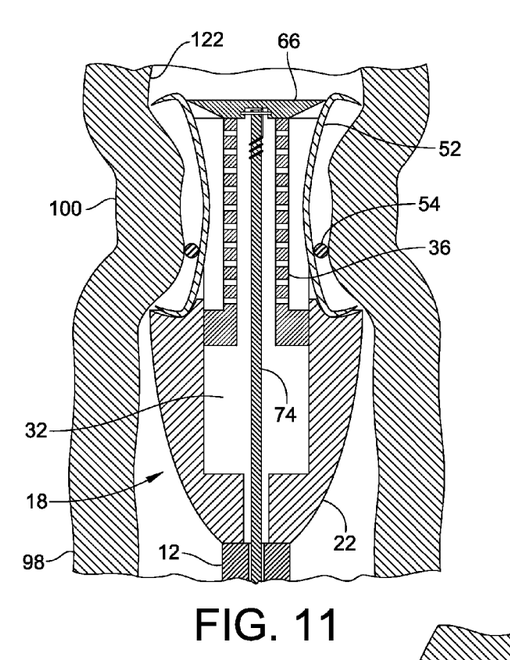
FIGS. 11 and 12 illustrate the progressive deformation of the staples within the gastric bander device.

To assemble the articulated shaft 12, one merely needs to stack the individual links 92 one on top of the other. The links 92 snap fit upon each other and self align themselves. A cable 74 is then passes through the interior passageway 94 and attaches to the anvil 66 as described above. A flexible and impervious membrane 96 is then placed over the articulated shaft 12 to render the articulated shaft 12 impermeable to air and to allow air to be suctioned from the stomach 100 in order to collapse the stomach 100 as illustrated in FIG. 10. Examples of the air impervious membrane 96 include PVC, Teflon, neoprene or other elastic film.

The operation of the gastric banding device 10 will now be explained with respect to FIGS. 9-16.

Referring to FIG. 9, the gastric bander device 10 is urged into the stomach 100 by insertion through the patient's esophagus 98. At the stage of placement, the cable 74 is extended and loose thereby rendering the articulated shaft 12 loose and articulatable. This allows the staple device 18 to move freely within the esophagus 98 until it reaches the stomach 100.

Once the staple device 18 is in place in the stomach 100, suction is applied by attaching a suction device (not illustrated) to the suction port 91 of the operations handle 20. By applying suction through the internal system, suction is thereby applied to the interior passageway 94 of the articulated shaft 12, the interior housing channel 32 of the housing 22 and the tube channel 46 of the slidable tube 36 which creates a vacuum causing air and gasses from the stomach 100 to pass through the suction ports 48 on the slidable tube 36. The suction action will cause the stomach 100 to deflate such that the internal wall 122 of the stomach 100 presses adjacent the exterior surface 38 of the slidable tube 36, as illustrated in FIG. 10.

Figure 12:
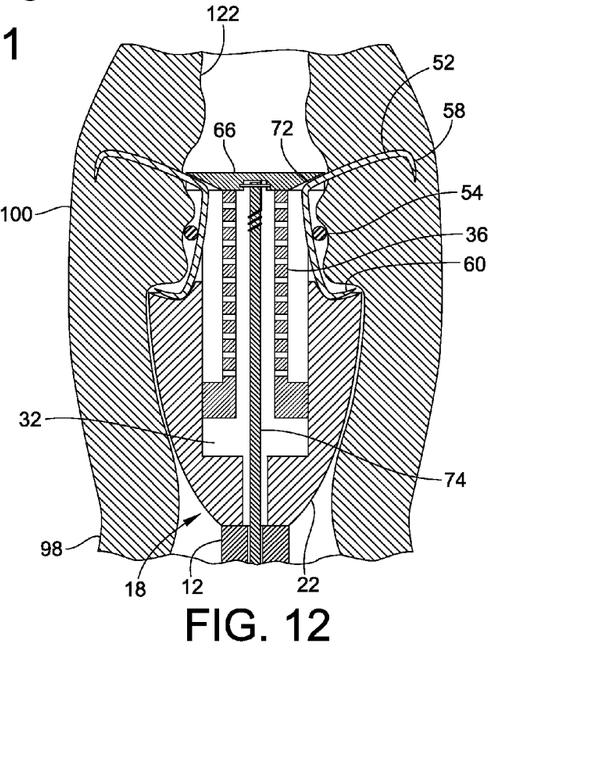
Figure 13:
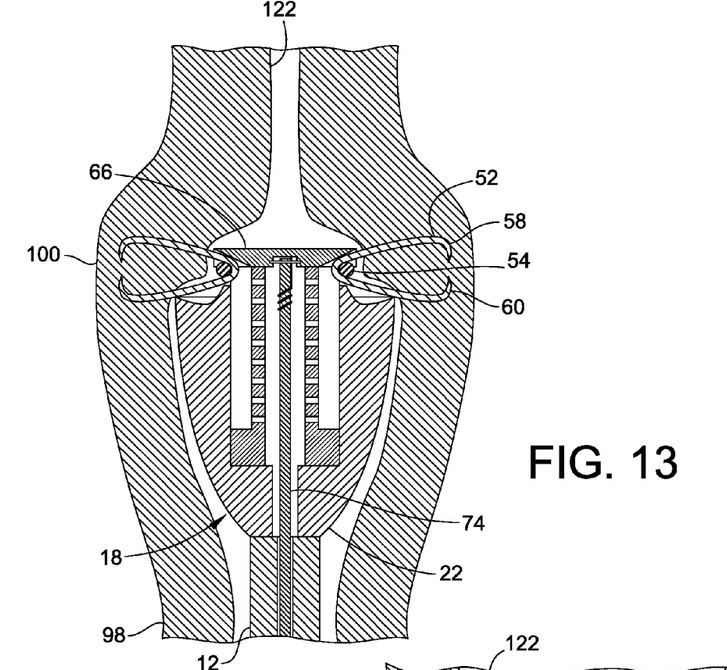
FIG. 13 illustrates the crimping and stapling of the constriction band to the stomach wall.

At this point, the cable 74 is tightened by the turn screw 82 to activate the staples 52. This progression is illustrated in FIGS. 10-13. As the cable 74 begins the tightening process, this causes the slidable tube 36 to slide within the interior housing channel 32. Because the constriction band 54 is removably attached to each of the staples 52, the constriction band 54 does not move with the slidable tube 36. The staple grooves 72 in the lower surface 70 of the anvil 66 assist the staple 52 in beginning its bending progression such that the first staple end 58 impinges upon the stomach lining 122. As the slidable tube 36 continues its progression into the interior housing channel 32, the staple continues to bend at its midpoint 57. As the slidable tube 36 continues to progress, as illustrated in FIG. 12, the second end 60 of the staple 52 begins a bending upward motion in the grooves 50 in the staple ring 62 at the first end 24 of the housing 22 until the staple 52 slides off of the staple ring 62 in the housing 22, piercing the interior wall 122 of the stomach 100 and eventually bending upon itself such that the ends 58 and 60 are nearly communicating with each other and grasping the stomach wall 122 as illustrated in FIG. 13-16. At this point, the constriction band 54 has been stapled to the stomach lining 122.

Once the constriction band 54 has been stapled to the stomach lining 122, the staple device 18 is removed from the stomach. Referring to FIGS. 14 and 15, the cable 74 is extended causing the anvil 66 to move in an outwardly fashion with respect to the upper first end 42 of the slidable tube 36. As illustrated in FIG. 14. The compression spring 79 will then cause the anvil 66 to rotate at a 90 degree angle such that the proportion of the lower surface 70 is adjacent the cable 74, as illustrated in FIGS. 14 and 15. At this point, the staple device 18 may be removed from the stomach 100 through the constriction band 54 and from the patient via the esophagus 98. Because the constriction band 54 is a resilient band, it tends to form an ovoid shape when released from the slidable tube 36. The ovoid shape will provide sufficient room for passage of the anvil 66.

Referring now to FIGS. 15 and 16, once the constriction band 54 is stapled in place on the stomach wall 122 and the stomach 100 is again inflated, a secondary pouch 124 is formed creating the restriction necessary to achieve desired weight loss. The constriction band 54 holds the stomach tissue inwardly, creating the secondary pouch 124.

This procedure is easily reversible by endoscopically cutting the constriction band 54, which is not itself attached to the stomach tissue. The constriction band 54 can then be removed from the stomach allowing the stomach 100 to conform to its original shape.

Preferred versions of the invention have been described above and below in order to illustrate how to make and use the invention, and the invention is not intended to be limited to these versions. The description set out above is merely of exemplary versions of the invention, and it is contemplated that numerous additions and modifications can be made. Nothing in this document should be construed as describing the only additions and modifications to the invention. The true scope of the invention will be defined by the claims.

It should be understood that various terms referring to orientation and position may be used throughout this document—e.g., the device entering down into the stomach—and that such terms are relative rather than absolute. Such terms should be regarded as words of convenience, rather than limiting terms. For example, if the patient is lying down during the procedure, the device may travel through the esophagus in a lateral or relatively horizontal rather than vertical orientation.

Any version of any component or method step of the invention may be used with any other component or method step of the invention. The elements described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference in their entirety to the same extent as if each individual reference were specifically and individually indicated as being incorporated by reference. In case of conflict between the present disclosure and the incorporated references, the present disclosure controls.

The devices, methods, compounds and compositions of the present invention can comprise, consist of, or consist essentially of the essential elements and limitations described herein, as well as any additional or optional steps, ingredients, components, or limitations described herein or otherwise useful in the art.

While this invention may be embodied in many forms, what is described in detail herein is a specific preferred embodiment of the invention. The present disclosure is an exemplification of the principles of the invention is not intended to limit the invention to the particular embodiments illustrated. It is to be understood that this invention is not limited to the particular examples, process steps, and materials disclosed herein as such process steps and materials may vary somewhat. It is also understood that the terminology used herein is used for the purpose of describing particular embodiments only and is not intended to be limiting since the scope of the present invention will be limited to only the appended claims and equivalents thereof.

What is claimed is:

1. A gastric bander staple device comprising:
   a. a housing having a first end and a second end and an interior housing channel;
   b. a slidable tube for slidable reception within the interior housing channel, the slidable tube having a first end, a second end, an exterior surface and an interior surface forming an open tube channel within the slidable tube;
   c. at least one suction port comprising an opening from the exterior surface of the slidable tube to the tube channel;
   d. a constriction band surrounding the exterior surface of the slidable tube,
   e. a plurality of staples removably positioned adjacent the exterior surface of the slidable tube and held in place by the constriction band; and
   f. an anvil removably positioned on the first end of the slidable tube, the anvil including a first upper surface and a second lower surface, wherein the second lower surface has a shape substantially similar to the first end of the slidable tube, the anvil further including a guide edge for the plurality of staples.

2. The staple device of claim 1 wherein the first end of the housing comprises a staple ring.

3. The staple device of claim 2 wherein the staple ring comprises outwardly extending staple grooves.

4. The staple device of claim 1 wherein the slidable tube includes a plurality of staple grooves, each staple groove adapted to removably receive a staple.

5. The staple device of claim 4 wherein each staple groove includes a plurality of suction ports.

6. The staple device of claim 1 wherein each staple of the plurality of staples has an elongated shaft having a first end and second end, wherein each end extends from the shaft at an approximately 90 degree angle, wherein further the shaft has a thinner area at a point on the shaft to facilitate flexure and bending of the staple.

7. The staple device of claim 1 wherein the guide edge of the anvil comprises a beveled edge between the first upper surface and the second lower surface of the anvil, wherein the beveled edge includes outwardly extending staple grooves, wherein the anvil further includes a notch.

8. The staple device of claim 1 further comprising a cable rotatably connected to the second lower surface of the anvil, wherein the cable further includes a compression spring for rotating the anvil.

9. The staple device of claim 1 wherein each of the plurality of staples comprises a first end and a second end, and wherein the plurality of staples are positioned with the first and second ends radially extending from the slidable tube.

10. A non-surgical gastric bander comprising:
    a. a staple device including
       i. a housing having a first end and a second end and an interior housing channel, wherein the first end of the housing comprises a staple ring comprising outwardly extending staple grooves;

ii. a slidable tube for slidable reception within the interior housing channel and having a first end, a second end, an exterior surface and an interior surface forming an open tube channel within the slidable tube, wherein the slidable tube includes a plurality of staple grooves, each staple groove adapted to removably receive a staple;

iii. at least one suction port comprising an opening from the exterior surface of the slidable tube to the tube channel;

iv. a constriction band surrounding the exterior surface of the slidable tube;

v. a plurality of staples removably positioned adjacent the exterior surface of the slidable tube and held in place by the constriction band; and vi. an anvil removably positioned on the first end of the slidable tube, the anvil including a first upper surface and a second lower surface, wherein the second lower surface has a shape substantially similar to the first end of the slidable tube, the anvil further including a guide edge for the plurality of staples;

b. an elongated, articulated shaft having a proximal end and a distal end, wherein the proximal end is connected to the first end of the housing, the articulated shaft being surrounded by an air impervious membrane;

c. an operations handle connected to the distal end of the articulated shaft, the operations handle comprising a suction port for attachment to a gas suction device;

d. a cable capable of being constricted and extended and having a proximal end and a distal end, wherein the proximal end is connected to the anvil and the distal end is connected to the operation handle.

11. The non-surgical gastric bander of claim 10 wherein each staple groove includes a plurality of suction ports.

12. The non-surgical gastric bander of claim 10 wherein each staple of the plurality of staples has an elongated shaft having a first and second end, wherein each end extends from the shaft at an approximately 90 degree angle, wherein further the shaft has a thinner area at a point on the shaft to facilitate flexure and bending of the staple.

13. The non-surgical gastric bander of claim 10 wherein the guide edge of the anvil comprises a beveled edge between the first upper surface and the second lower surface of the anvil, wherein the beveled edge includes outwardly extending staple grooves, wherein the anvil further includes a notch on the beveled edge.

14. The non-surgical gastric bander of claim 10 wherein the articulated shaft comprises a plurality of adjacent links, wherein each link is pivotally attached to an adjacent link in a manner to allow limited pivoting movement of the shaft in both an X and a Y axis, a. wherein each link comprises an outer surface, an inner surface forming an interior passageway, an upper first surface comprising an arched protrusion including a pair of outwardly extending lips, and a lower second surface comprising an arched notch comprising a pair of inwardly depending edges wherein the pair of outwardly extending lips of the upper first surface are formed to receive the pair of inwardly depending edges of the next adjacent link in a snap fit fashion to connect each adjacent link in a manner allowing limited pivoting movement of the connected adjacent links in both an X and a Y axis, and b. wherein the articulated shaft further comprises a cable capable of being constricted and extended and having a proximal and a distal end, wherein the proximal end of the cable is connected to a stopper mechanism at the proximal end of the articulated wherein constriction of the cable prevents pivotal movement of adjacent links with respect to each other and extension of the cable allows pivotal movement of adjacent links.

15. The non-surgical gastric bander of claim 14 wherein the upper first surface and/or the lower second surface of each link is beveled to assist in the pivotal movement of each adjacent link.

16. The non-surgical gastric bander of claim 14 wherein the upper first surface and lower second surface of each link are defined by a roughened or knurled surface to assist in prevention of pivotal movement of adjacent links when the cable is constricted.

17. The non-surgical gastric bander of claim 10 wherein each of the plurality of staples comprises a first end and a second end, and wherein the plurality of staples are positioned with the first and second ends radially extending from the slidable tube.

* * * * *